United States Patent [19]

Patton

[11] Patent Number: 4,577,624

[45] Date of Patent: Mar. 25, 1986

[54] HYDROMASSAGE AND WHIRLPOOL BATH

[76] Inventor: Larry Patton, 38 Guardsman Rd., Thornhill, Ontario, Canada

[21] Appl. No.: 621,258

[22] Filed: Jun. 15, 1984

Related U.S. Application Data

[63] Continuation-in-part of Ser. No. 416,955, Sep. 13, 1982, abandoned.

[51] Int. Cl.[3] ........................................ A61N 1/100

[52] U.S. Cl. .................................... 128/40; 128/66; 128/369; 119/158

[58] Field of Search .................... 128/540, 52, 62, 66, 128/365-369; 119/158, 159, 29, 1; 4/541, 542

[56] References Cited

U.S. PATENT DOCUMENTS

| | | | |
|---|---|---|---|
| 3,155,072 | 11/1964 | Owens | 119/1 |
| 3,420,226 | 1/1969 | Berry, Sr. | 128/369 |
| 3,772,714 | 11/1973 | Sealby et al. | 4/541 |
| 3,874,374 | 4/1975 | Jacuzzi | 128/66 |
| 4,155,878 | 9/1978 | Johnson et al. | 128/66 |
| 4,183,329 | 1/1980 | Leonaggeo, Jr. | 119/158 |
| 4,225,984 | 10/1980 | Lindsey | 128/66 |
| 4,340,039 | 7/1982 | Hibbard et al. | 4/542 |
| 4,341,183 | 7/1982 | Metzler | 128/66 |
| 4,379,438 | 4/1983 | Peardon | 119/158 |

*Primary Examiner*—Richard J. Apley
*Assistant Examiner*—H. Macey

[57] ABSTRACT

Portable water massage for massaging the legs of four legged animals, particularly horses, the massage mechanism consists of four multi-directional jets situated in a specific configuration, the jets direct a mixture of water and air into a container adapted to receive a leg of the horse.

2 Claims, 5 Drawing Figures

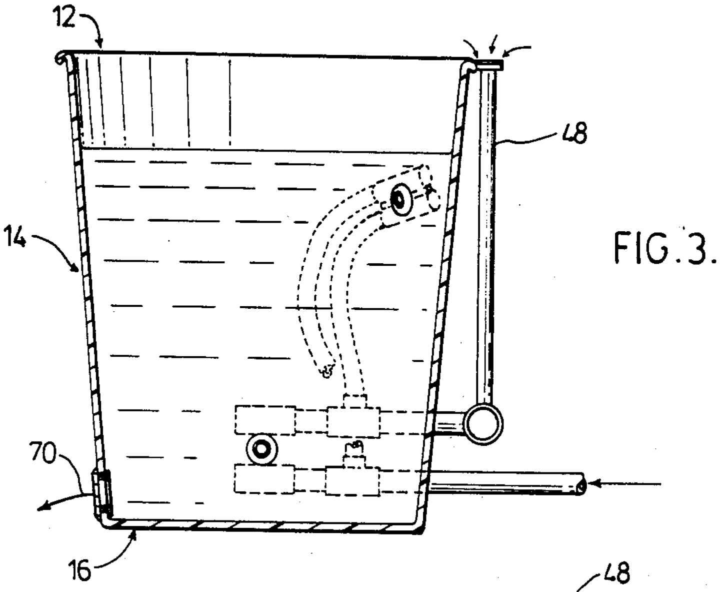
FIG. 3.
FIG. 2.
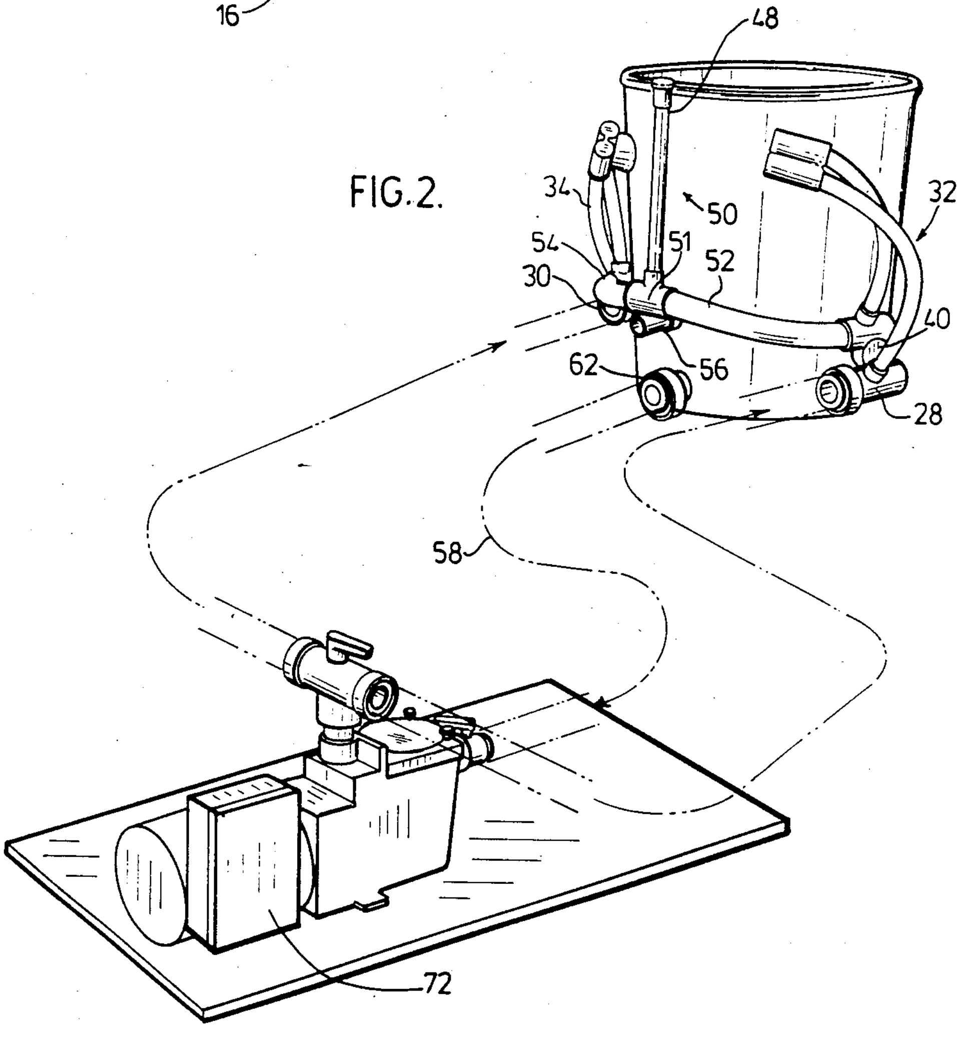

FIG. 4.
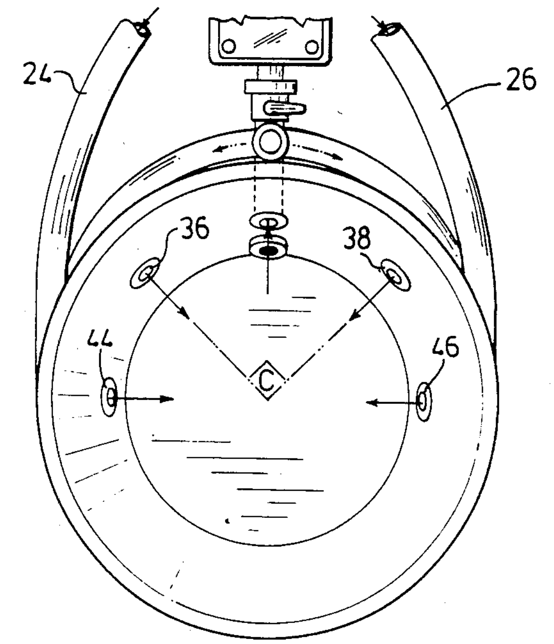
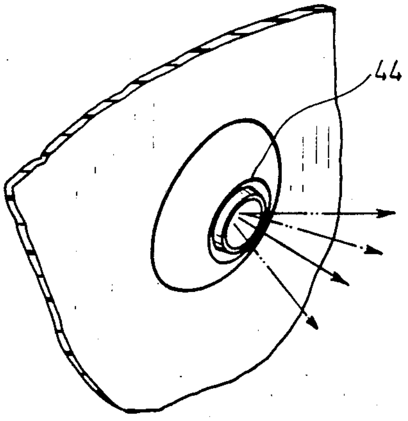
FIG. 5.

HYDROMASSAGE AND WHIRLPOOL BATH

This application is a continuation-in-part application of U.S. patent application Ser. No. 416,955 filed Sept. 13, 1982, now abandoned.

FIELD OF INVENTION

This invention relates to water massages for massaging the legs of four legged animals, and finds particular application to water massages for horses.

BACKGROUND OF THE INVENTION

Because of the vulnerability of the legs of horses, it is essential that all minor leg irritations or problems are immediately attended to, to preclude further deterioration. In fact, because of their vulnerability, the legs must be attended to after every workout. To this end, a hydromassage and whirlpool bath is proposed. Particularly, the jets ejecting the mixture of water and air are applied to the points of most strain on the horse's legs. However, the application must not be such as to overpower in any one area and underapply in another.

It is therefore an object of this invention to provide such hydromassage and whirlpool bath which ensures effective treatment under all circumstances.

It is a further object of the invention to provide such a bath which is readily portable and accessible for use.

Further and other objects of the invention will be realized by those skilled in the art from the following summary of the invention and detailed description of a preferred embodiment thereof.

SUMMARY OF THE INVENTION

According to one aspect of the invention, a hydromassage and whirlpool bath for massaging the legs of a four legged animal is provided, comprising:

(a) a bath container having a center, a bottom and a peripheral upstanding wall formation made from yieldable plastics material, the wall formation upstanding from the bottom and enclosing the bath container;

(b) a water suction outlet from the bath container secured to the pump for returning water to the pump through the lower part of the bath container;

(c) four jets secured in the bath, two proximate the bottom and two proximate the top of the wall formation, the jets being multi-directional for directing a mixture of water and air into the bath, the two lower jets being substantially diametrically opposed on the peripheral wall formation equally spaced from the water suction outlet for massaging the pastern, ankle and tendon extending from the ankle to the back of each knee, the two upper jets being circumferentially disposed between the two lower jets on either side of the outlet, the circumferential distances between one of the upper jets and the lower jet closest to it and the other upper jet and the lower jet closest to it being about equal, the upper jets forming together with the center of the bath, an angle of about 90° and the distance between one of the lower jets and the outlet and the other lower jet and the outlet being about equal and the distance between one of the upper jets and the outlet and the other upper jet and the outlet being about equal, the upper jets for massaging the area of the leg proximate the cannon bone, knee and forearm;

(d) a pump;

(e) an air injector secured to tubing carrying water to the bath for injecting air into the water circulated by the pump for passage through the jets;

(f) tubing secured to the air injector, pump, suction outlet and jets for pumping the mixture of air and water through the jets disposed about a circumferential bath container portion proximate the jets and suction outlet while leaving the circumferential portion opposite the outlet and the upper jets clear; and (g) a motor for operating the pump positioned on the side of the container closer the outlets and jets.

Preferably, the bottom jets are larger than the upper jets and preferably each of the jets comprises multi-directional "eye ball" outlets to direct the water where desired.

Preferably, the bath comprises two suction outlets, one above the other with the lower outlet proximate the bottom of the container. When the pump is located proximate the bath, tubing connecting the pump and the bath are secured to the upper suction outlet. When the pump is located farther from the bath, (for example, about ten feet), the lower suction outlet is secured by tubing to the pump rather than the upper outlet. The use of this lower outlet ensures an adequate flowrate of water through the bath by compensating for the expected decrease in the flowrate of the water if the upper suction outlet had been used by initial greater force on the water entering the tubing from the bath.

In use, the horse is brought to the end of the bath remote that portion of the bath wall in which the jets are not mounted, and the horse is "walked" into the bath (the front legs stepping over the portion of the peripheral bath wall without the jets or the rear legs stepping over the portion of the peripheral bath wall without the jets as the case may be.

BRIEF DESCRIPTION OF THE DRAWINGS

The invention will now be illustrated with reference to the following drawings of preferred embodiments in which:

FIG. 2 is a perspective view of the structure shown in FIG. 1, with component parts spaced from one another and connected by tubing of greater length than that used in FIG. 1.

FIGS. 1 and 3 are side sectional views of part of the structure shown in FIG. 3.

FIG. 4 is top view of the structure shown in FIGS. 1 and 3.

FIG. 5 is a close-up view of part of the structure shown in FIG. 4.

DETAILED DESCRIPTION OF THE DRAWINGS

Figure 1:
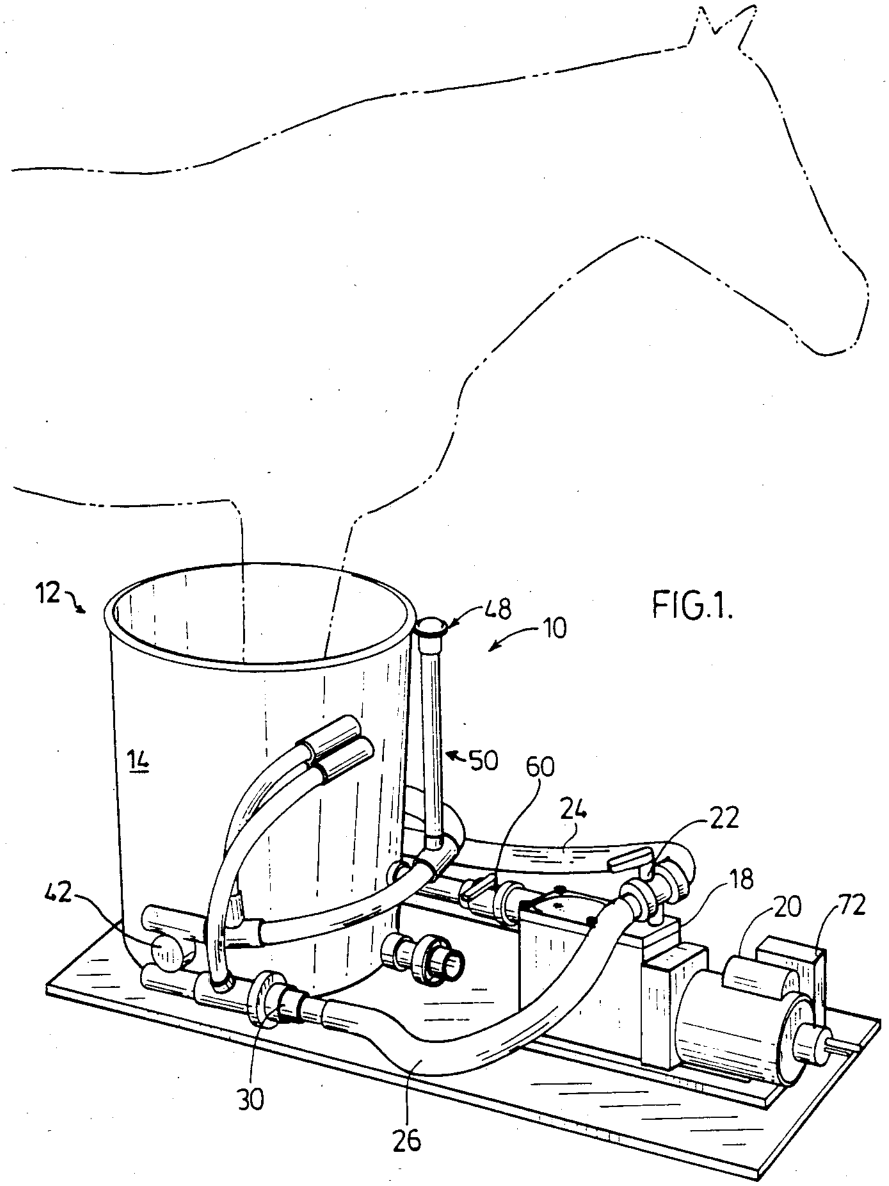
FIG. 1 is a perspective view of a hydromassage and whirlpool bath according to the preferred embodiment of the invention being used to massage and sooth the front legs of a horse.

With reference to FIG. 1, there is shown hydromassage and whirlpool bath 10, comprising inverted truncated conically shaped low density polyethylene tub 12, having upstanding side wall formation 14 and bottom 16, pump 18 (Model SP-1605 manufactured by Hayward Manufacturing Co. Inc.) with lint and hair strainer, (not shown), operated by electric waterproof motor 20, four way valve 22 secured to pump 18 to control water flow and having inlets secured to flexible lengths of PVC pipe 24 and 26 secured by connectors 28 and 30, in turn secured by tubing 32 and 34 respectively, (See FIG. 2) to upper hydro jets 36 and 38 and by tubing 40 and 42 to lower hydrojets 44 and 46 (See also FIG. 4).

Suction fitting assembly 48 (air control valve) is secured to such air through air control assembly 50 through T-connector 51, tubing 52 and 54 and secured to hydro jets 36, 38, 44 and 46 for mixture with the water pumped through the pump.

With reference to FIG. 4, the configuration of the hydro jets 36, 38, 44 and 46 are such that jets 44 and 46 are diametrically opposed one another adjacent to the bottom to direct the air-water mixture at the horse's pastern, ankle, and tendon extending from the ankle to the back of the knee, and that upper jets 36 and 38 forming with the center (c) of the container an angle of 90°, the circumferential distances between jets 44 and 36 and jets 38 and 46 being about equal. Both the upper and lower jets comprise directional "eye balls" (See FIG. 5) for multi-directional use. The lower jets 44 and 46 are larger (5/16") than the upper jets 36 and 38 (¼") permitting a greater volume of flow therethrough.

Water suction outlet 56 returns fluid through PVC tubing through two-way control valve 60 to pump 18 (through filter not shown) as shown in FIG. 1. When it is desired to space the pump and motor assembly from the bath, (See FIG. 2) larger PVC tubing 58 is then secured to water suction outlet 62 secured to pump 18 by tubing 58. In this case, the use of lower suction outlets 62 ensures the adequate flow rate of the water from the bath when the pump is spaced a greater distance from the bath as in FIG. 4. When suction outlets 56 and 62 are not in use, one or the other is appropriately capped. Drain 70 is provided for draining the bath when not in use.

In use, a horse is walked to the bath, the front or back legs put into the container over the wall portion not containing the jets, and the bath turned on. The "eye balls" are appropriately adjusted and the flow controlled.

For electrical security, ground fault interrupter 72 is provided.

As many changes could be made to the structure of the preferred embodiments without departing from the scope of the invention, it is intended that all matter contained herein be interpreted as illustrative of the invention and not in a limiting sense.

I claim:

1. A hydromassage and whirlpool bath for massaging the legs of four legged animals, comprising:

(a) a bath container having a center, a bottom and peripheral upstanding wall formation made from yieldable plastics material, the wall formation upstanding from the bottom and enclosing the bath container;

(b) a water suction outlet secured to the lower part of the peripheral wall;

(c) massage means consisting of four multi-directional jets secured to the bath, two proximate the bottom and two proximate the top of the wall formation the jets for directing a mixture of water and air into the bath, the two lower jets being substantially diametrically opposed on the peripheral wall formation equally spaced from the water suction outlet, the other two jets being circumferentially disposed between the two lower jets on either side of the outlet, the circumferential distances between one of the upper jets and the nearest lower jet to it, and the other upper jet and nearest lower jet to it being about equal, the upper jets forming together with the center of the bath, an angle of about 90° and the distance between one of the lower jets and the outlet and the other lower jet and the outlet being about equal, and the distance between one of the upper jets and the outlet and the other upper jet and the outlet being about equal;

(d) a pump adjacent to the bath container provided with means comprising tubing to pump water through the jets in the bath;

(e) an air injector means secured to the tubing carrying water to the bath for injecting air into the water;

(f) further tubing connecting the suction outlet to the pump and (g) a motor secured to the pump for operating the pump.

2. The hydromassage and whirlpool bath of claim 1, wherein the bottom jets are larger than the upper jets.

* * * * *

UNITED STATES PATENT AND TRADEMARK OFFICE
CERTIFICATE OF CORRECTION

PATENT NO. : 4,577,624

DATED : March 25, 1986

INVENTOR(S) : Larry Patton

It is certified that error appears in the above-identified patent and that said Letters Patent is hereby corrected as shown below:

At column 3 of the patent, line 5 after 'to' and before 'air', the word "such" has been replaced with ---suck---.

Signed and Sealed this

Third Day of January, 1989

*Attest:*

DONALD J. QUIGG

*Attesting Officer*

*Commissioner of Patents and Trademarks*